United States Patent
Lee

(10) Patent No.: US 11,948,294 B2
(45) Date of Patent: Apr. 2, 2024

(54) DEVICE AND METHOD FOR SUPPORTING BONE MARROW READING BASED ON IMAGE ANALYSIS

(71) Applicant: UIMD INC., Seoul (KR)

(72) Inventor: Young Deuk Lee, Seoul (KR)

(73) Assignee: UIMD INC., Seoul (KR)

( * ) Notice: Subject to any disclaimer, the term of this patent is extended or adjusted under 35 U.S.C. 154(b) by 512 days.

(21) Appl. No.: 17/162,070

(22) Filed: Jan. 29, 2021

(65) Prior Publication Data

US 2021/0158516 A1 May 27, 2021

Related U.S. Application Data

(63) Continuation of application No. PCT/KR2019/007194, filed on Jun. 14, 2019.

(30) Foreign Application Priority Data

Aug. 2, 2018 (KR) .................. 10-2018-0090182

(51) Int. Cl.
  G06T 7/00 (2017.01)
  A61B 5/00 (2006.01)
  G16H 50/30 (2018.01)

(52) U.S. Cl.
  CPC ............ G06T 7/0012 (2013.01); A61B 5/417 (2013.01); A61B 5/7267 (2013.01); G16H 50/30 (2018.01); *G06T 2207/30004* (2013.01)

(58) Field of Classification Search
  CPC ...... G06T 7/0012; G16H 50/30; A61B 5/417; A61B 5/7267
  See application file for complete search history.

(56) References Cited

U.S. PATENT DOCUMENTS

| 8,238,627 B2 | 8/2012 | Homman et al. |
| 9,760,689 B2 | 9/2017 | Chang et al. |
| 2013/0094750 A1* | 4/2013 | Tasdizen ............... G06V 20/695 382/134 |
| 2014/0370525 A1* | 12/2014 | Weiss ............... G01N 33/57426 435/7.25 |

(Continued)

FOREIGN PATENT DOCUMENTS

| CN | 107977684 A | 5/2018 |
| KR | 10-2008-0060219 A | 7/2008 |

(Continued)

OTHER PUBLICATIONS

International Search Report and Written Opinion, PCT/KR2019/007194, dated Sep. 3, 2019, 13 pages.

(Continued)

*Primary Examiner* — David Bilodeau
(74) *Attorney, Agent, or Firm* — United One Law Group LLC; Kongsik Kim; Jhongwoo Peck

(57) ABSTRACT

A device for supporting bone marrow reading based on image analysis includes an image acquisition unit for acquiring a bone marrow image of a subject for bone marrow reading by an imaging device; a discrimination index unit for classifying the acquired bone marrow image into a class among a plurality of classes corresponding to preset discrimination indices; and a result providing unit for providing the result read by the discrimination index unit.

12 Claims, 6 Drawing Sheets

(56) References Cited

U.S. PATENT DOCUMENTS

| | | | | |
|---|---|---|---|---|
| 2018/0318303 | A1* | 11/2018 | Trehu | A61K 38/202 |
| 2019/0347467 | A1* | 11/2019 | Ohsaka | G06V 10/449 |
| 2020/0150021 | A1* | 5/2020 | Ohsaka | G16H 50/30 |
| 2020/0211182 | A1* | 7/2020 | Nagasaka | G06V 10/82 |
| 2021/0027890 | A1* | 1/2021 | Fu | G16H 50/30 |

FOREIGN PATENT DOCUMENTS

| | | | |
|---|---|---|---|
| KR | 10-2009-0006295 | A | 1/2009 |
| KR | 10-2013-0101867 | A | 9/2013 |
| KR | 10-2014-0063288 | A | 5/2014 |
| KR | 10-1857624 | B1 | 5/2018 |
| WO | 2020027431 | A1 | 2/2020 |

OTHER PUBLICATIONS

Extended European Search Report for counterpart European Application No. 19843366.6, dated Sep. 7, 2021.

Bagasjvara et al., "Automated Detection and Classification Techniques of Acute Leukemia using Image Processing: A Review," 2016 2nd International Conference on Science and Technology-Computer (ICST), Oct. 27, 2016, pp. 35-43, IEEE, Yogyakarta, Indonesia.

Kainz et al., "Training echo state networks for rotation-invariant bone marrow cell classification," Neural Computing & Applications, Sep. 21, 2016, vol. 28, No. 6, pp. 1277-1292, Springer London.

Diaz et al., "Automatic Analysis of Microscopic Images in Hematological Cytology Applications," Automatic Analysis of Microscopic Images in Hematological Cytology Applications, Dec. 31, 2009, pp. 1-26, HAL.

Krappe et al., "Automated classification of bone marrow cells in microscopic images for diagnosis of leukemia: a comparison of two classification schemes with respect to the segmentation quality," Medical Imaging 2015: Computer-Aided Diagnosis, Mar. 20, 2015, vol. 9414, No. 941431, pp. 1-6, Proc. of SPIE.

* cited by examiner

DEVICE AND METHOD FOR SUPPORTING BONE MARROW READING BASED ON IMAGE ANALYSIS

CROSS-REFERENCE TO RELATED APPLICATIONS

This application is a Continuation of International Application No. PCT/KR2019/007194 filed on Jun. 14, 2019, which claims priority to Korean Application No. 10-2018-0090182 filed on Aug. 2, 2018. The aforementioned applications are incorporated herein by reference in their entireties.

TECHNICAL FIELD

The present disclosure relates to a device and a method for supporting bone marrow reading, and more particularly, for supporting bone marrow reading based on image analysis capable of more efficiently and more easily performing bone marrow reading by providing images used for bone marrow reading and classifying bone marrow cells into different classes for each type to provide discrimination indices.

RELATED ART

Bone marrow examination is one of diagnostic testing methods performed by collecting bone marrow, which is a hematopoietic organ. Such bone marrow examination is performed not only for diagnosis of various blood diseases and follow-up tests after treatment, but also to determine whether various cancers have metastasis to the bone marrow, and to determine whether granulomatous diseases such as tuberculosis are invaded.

To read the bone marrow examination results, diagnostic hematologists diagnose by examining stained bone marrow smear samples and bone marrow biopsy tissue sections under a microscope and formulating the discrimination indices of bone marrow cells. In addition, if necessary, a comprehensive diagnosis should be made by examining various types of specially stained smear slides or immunostained biopsy tissue section slides. This task requires substantial experience and knowledge, and results in severe eye fatigue as it is necessary to observe various parts of the slide at high magnification and the examining doctor is required to spend an extended amount of time.

In addition, if it is difficult to read the bone marrow, it is necessary to ask for opinions of other experts. However, currently, there is an inconvenience in that the bone marrow slides are packaged and sent by parcel post or courier service, the bone marrow slides are observed again under a microscope by the party who received the bone marrow slides, the results are sent by wired communication or by paper, and the slides are returned. Due to the inconvenience and time consumption, there is a problem in that the necessary information cannot be delivered to a clinical doctor treating a patient on the day of the examination.

In the related art, in order to use a bone marrow image, a person is required to take a microscopic picture, but since the image quality is poor and only the cells in a part that the observer wants are imaged, this method alone is unable to be used for diagnosis. In addition, a method of training a bone marrow reading is limited to apprenticeship, which has many limitations that require using a microscope together, and even if there is an atlas, only a few stereotypical cell type photographs are available. For the same reason, there is no quality control method to determine whether the bone marrow examination is properly read.

The above-described technical configuration is the background art for assisting the understanding of the present disclosure, and does not constitute a prior art technology.

SUMMARY

The present disclosure has been made in an effort to provide a device for supporting bone marrow reading based on image analysis capable of providing all images used for bone marrow reading in sufficient numbers at a required magnification using an image analyzer, capturing bone marrow cells with five hundred images or a number specified by a client at high magnification to provide the images that are classified into different classes for each cell type using an algorithm, and thus enhancing the efficiency and convenience of bone marrow reading by providing the images in this manner.

According to an aspect of the present disclosure, a device for supporting bone marrow reading based on image analysis may include an image acquisition unit configured to acquire, by an imaging device, a bone marrow image of a subject for bone marrow reading; a discrimination index unit configured to generate a required image from the acquired bone marrow image by image processing and software operation and classify the acquired bone marrow image into a class among a plurality of classes corresponding to discrimination indices by a preset algorithm; and a result providing unit configured to provide the required image and discrimination result that is read by the discrimination index unit.

The required image may include a large particle having a size larger than sizes of other particles in a vicinity thereof in a whole bone marrow image screen.

The required image may include the large particles and megakaryocytes that are present in a zone of interest in front of and behind the large particles.

The result providing unit may provide both the required image and a discrimination index corresponding to a class to which the required image belongs.

The present disclosure may further include a database unit configured to store a plurality of bone marrow images classified based on preset discrimination indices, and the result providing unit may provide both data analyzed by the discrimination index unit and data stored in the database unit.

According to another aspect of the present disclosure, a method of supporting bone marrow reading based on image analysis may include acquiring, by an imaging device, a bone marrow image of a subject for bone marrow reading; generating a required image from the acquired bone marrow image by image processing; classifying the acquired bone marrow image into a class among a plurality of classes that correspond to discrimination indices based on a preset algorithm; and providing the required image and a discrimination result.

According to another aspect of the present disclosure, a non-transitory computer readable medium containing program instructions executed by a processor or controller. The program instructions when executed by the processor or controller may be configured to cause an imaging device to acquire a bone marrow image of a subject for bone marrow reading; generate a required image from the acquired bone marrow image by image processing; classify the acquired bone marrow image into a class among a plurality of classes that correspond to discrimination indices based on a preset algorithm; and provide the required image and a discrimination result.

According to the present disclosure, the device for supporting bone marrow reading based on image analysis having the configuration as described above may classify all the bone marrow images acquired by an imaging means such as Computerized Tomography (CT) into a class among a plurality of classes corresponding to discrimination indices, and provide them. Accordingly, the present disclosure provides advantages of saving labor and time by performing bone marrow reading without microscopic observation, enabling consultation with other experts or remote reading at a place such as a central reading center by reading the bone marrow images by discrimination indices based on an algorithm for discrimination of bone marrow cells, and providing educational data of a complete image set to train bone marrow reading doctors.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION

Hereinafter, exemplary embodiments of the present disclosure will be described in detail with reference to the accompanying drawings and the contents disclosed in the accompanying drawings, but the present disclosure is not limited or restricted to the exemplary embodiments.

Various modifications may be made to embodiments to be described below. Embodiments to be described below are not intended to be limited to aspects and should be understood to include all modifications, equivalents, and substitutes thereof.

Terminologies used herein are used only to describe specific embodiments, and are not intended to limit the embodiments. A singular form may include a plural form unless otherwise clearly meant in the context. Further, in the present application, it should be understood that the term "including" or "having" indicates that a feature, a number, a step, an operation, a component, a part or the combination thereof described in the specification is present, but does not exclude a possibility of presence or addition of one or more other features, numbers, steps, operations, components, parts or combinations thereof, in advance.

Meanwhile, in describing the present disclosure, detailed description of related known function or configuration will be omitted if it is determined that they unnecessarily obscure the gist of the present disclosure. Terminologies herein are used to properly describe embodiments of the present disclosure, which may vary depending on a user, an operator's intention, or customs in the art to which the present disclosure pertains. Accordingly, definitions of the terminologies need to be described based on contents throughout this specification.

In describing the embodiments, a detailed description of related known technologies will be omitted if it is determined that they unnecessarily obscure the gist of the embodiments.

Figure 1:
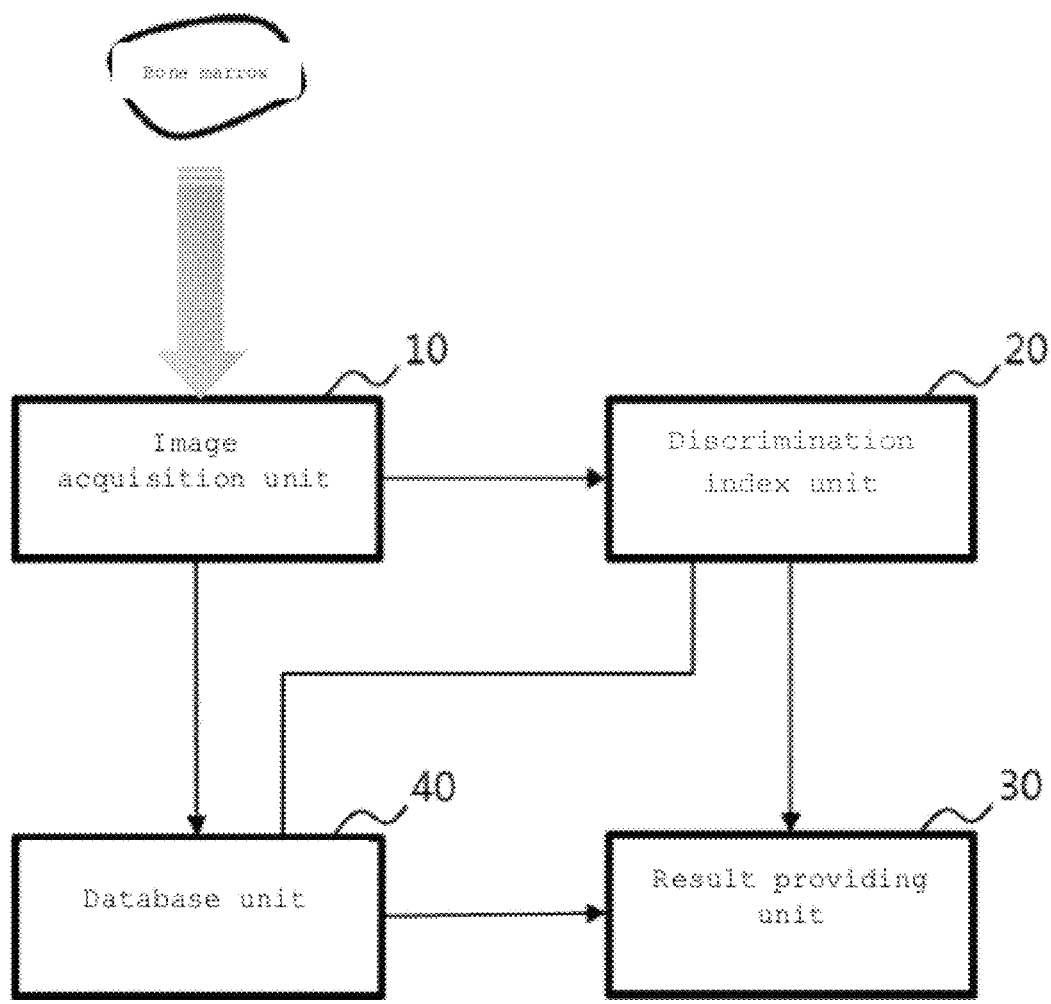
FIG. 1 is a schematic diagram for describing a configuration of a device for supporting bone marrow reading based on image analysis according to an embodiment of the present disclosure.
Figure 2:
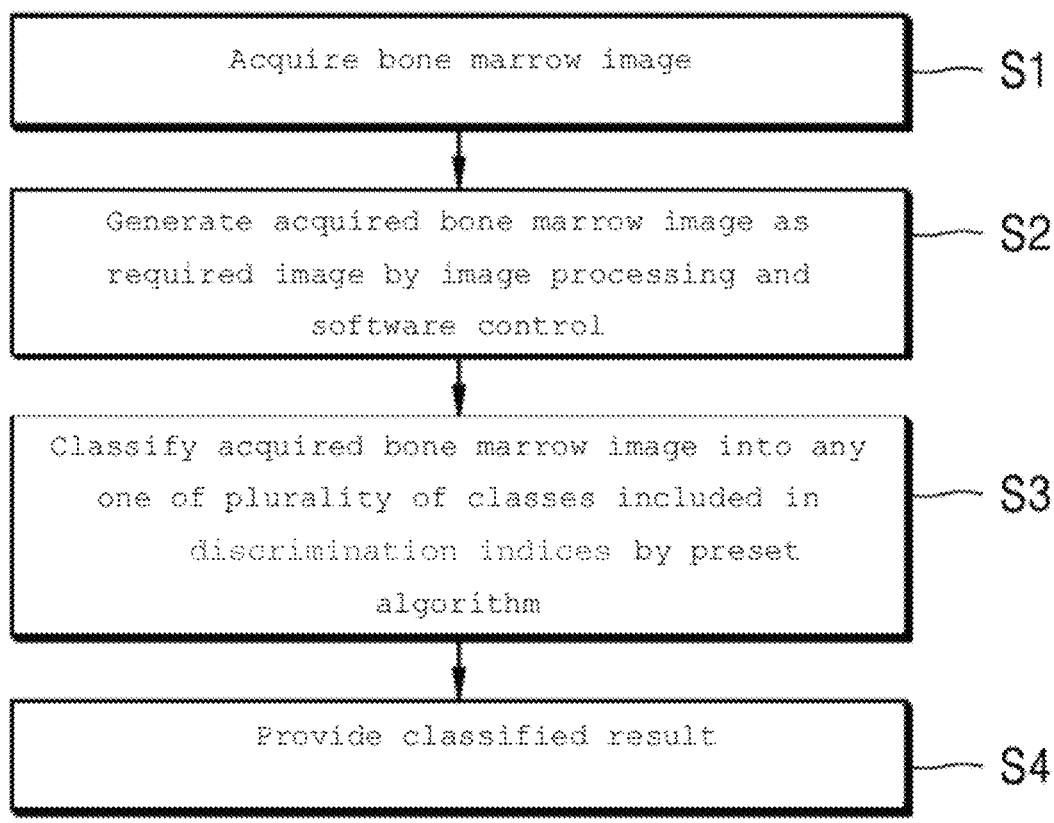
FIG. 2 is a flowchart sequentially illustrating a process according to an embodiment of the present disclosure.
Figure 3:
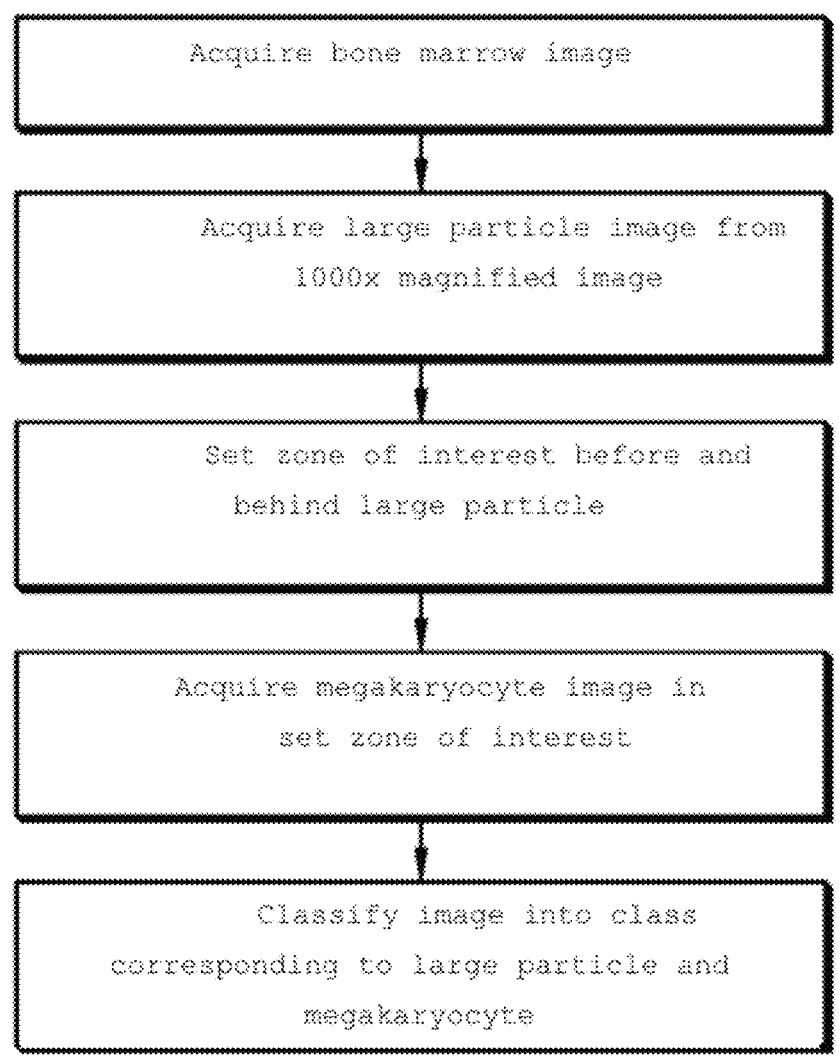
FIG. 3 is a flowchart sequentially illustrating a reading process of a discrimination index unit according to an embodiment of the present disclosure.
Figure 4:
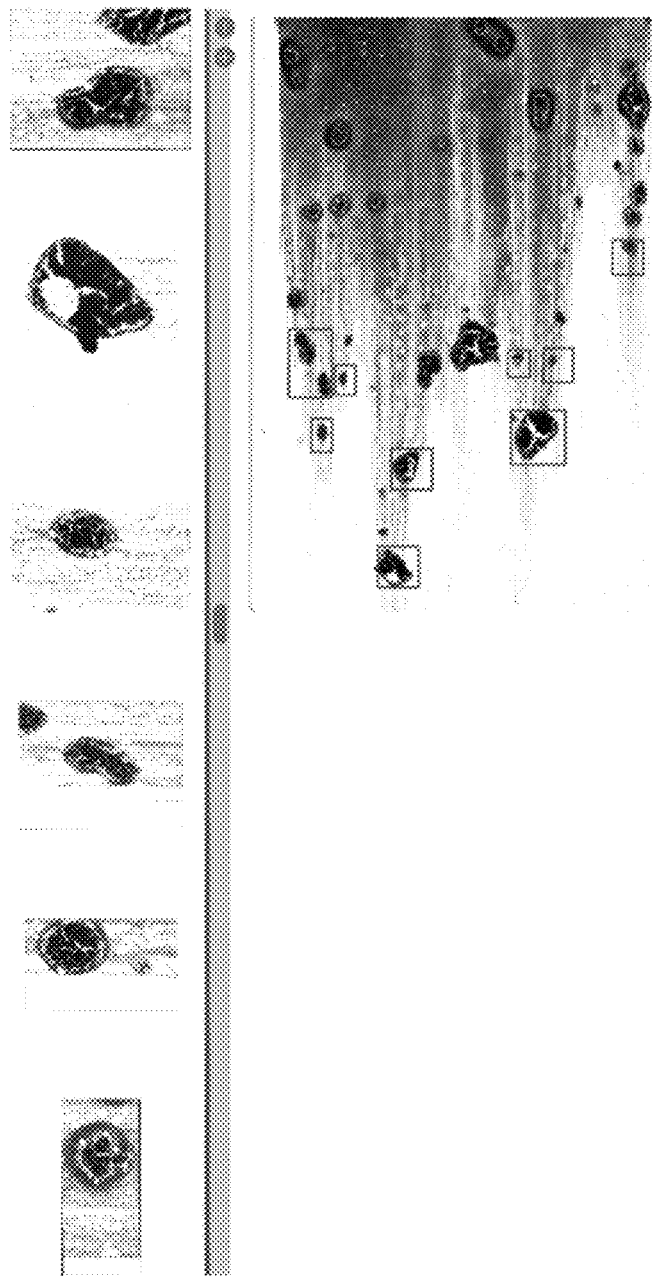
FIG. 4 shows an example of an image acquired by an image acquisition unit according to an embodiment of the present disclosure.
Figure 5:
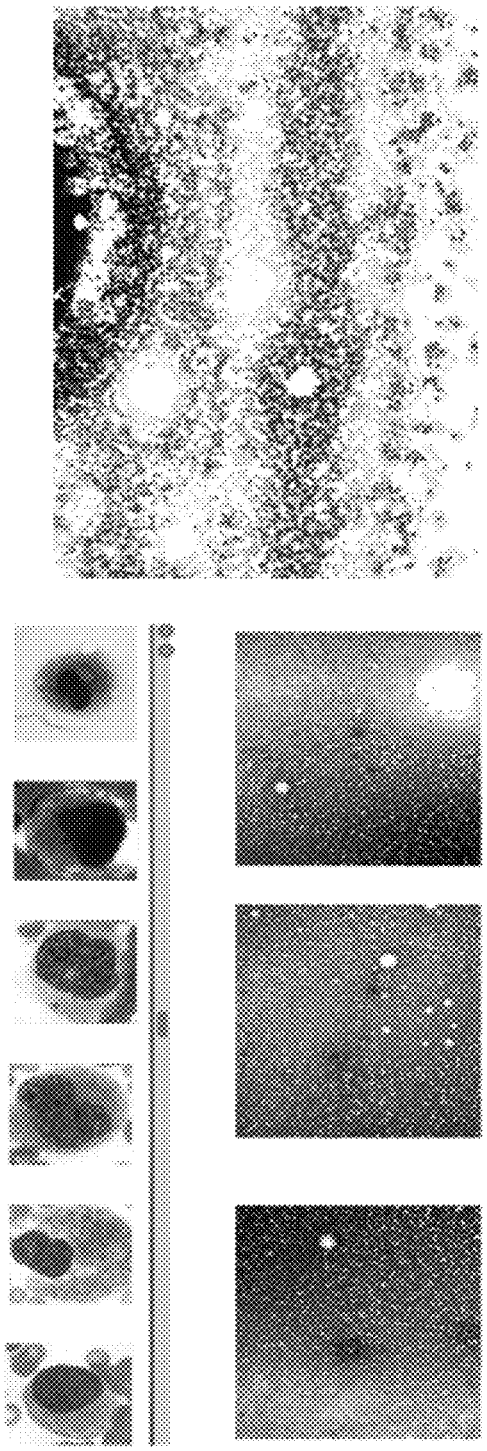
FIG. 5 shows an enlarged photograph of an image around a large particle in FIG. 4.
Figure 6:
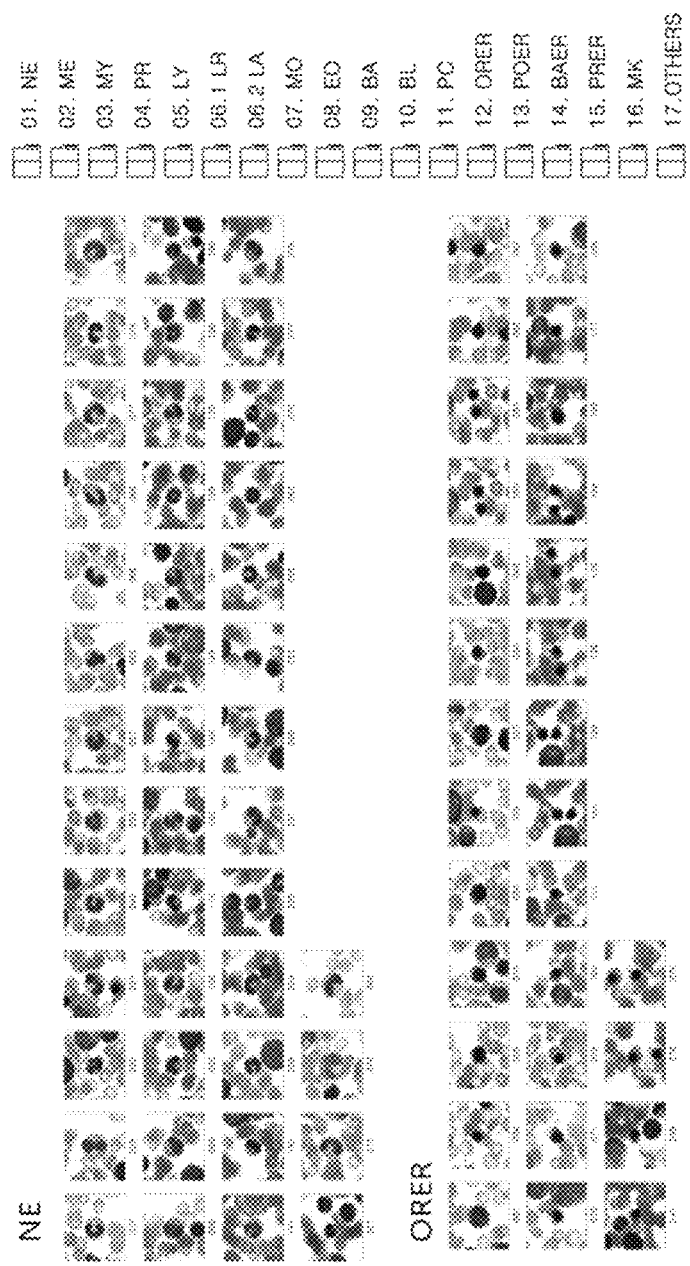
FIG. 6 shows a photograph of an example of a result provided by a result providing unit according to an embodiment of the present disclosure.

FIG. 1 is a schematic diagram for describing a configuration of a device for supporting bone marrow reading based on image analysis according to an embodiment of the present disclosure, FIG. 2 is a flowchart sequentially illustrating a process according to an embodiment of the present disclosure, FIG. 3 is a flowchart sequentially illustrating a reading process of a discrimination index unit 20 according to an embodiment of the present disclosure, FIG. 4 shows an example of an image acquired by an image acquisition unit 10 according to an embodiment of the present disclosure, FIG. 5 shows an enlarged photograph of an image around a large particle in FIG. 4, and FIG. 6 shows a photograph of an example of a result provided by a result providing unit 30 according to an embodiment of the present disclosure.

As illustrated in FIGS. 1 and 2, the device for supporting bone marrow reading based on image analysis according to an embodiment of the present disclosure includes an image acquisition unit 10, a discrimination index unit 20, and a result providing unit 30.

The image acquisition unit 10 acquires images of bone marrow cells such as shown in FIGS. 4 and 5 using an imaging means such as CT (S1) to capture and provide all images used for bone marrow reading to a doctor.

The discrimination index unit 20 generates a required image from the acquired bone marrow image, such as shown in FIGS. 4 and 5, by image processing and software operation (S2), and classifies the acquired bone marrow image into any one of a plurality of classes included in discrimination indices by a preset algorithm (S3).

For example, the required image may be a large particle having a size larger than sizes of other particles around it across a whole bone marrow image screen. According to the embodiment of the present disclosure, a specified number of required images are captured and provided for the large particles.

In some embodiments, cells that are present in front of and behind the large particles in a zone of interest are generated as required images together with the large particles. A specified number of required images are configured to be provided. For example, for determining megakaryocytes, a sufficient size is defined in front of the particles are captured and provided in the specified number, and the megakaryocytes are detected with software and the high-magnification images are captured and provided.

The discrimination index of the bone marrow cell is an index that is determined by a cell classification algorithm using the high-magnification cell images acquired from a region where the cells are well-smeared, and the result providing unit 30 provides the discrimination indices together with the required images (S4).

For example, when a slide of the bone marrow specimen is a specially-stained smear slide, the result providing unit 30 may be configured to provide a specified number of particle images, zone-of-interest images, and high-magnification cell images. In addition, the number of provided images may be set by the client. Entire images of bone marrow tissue sections are provided for general staining, immunostaining, and special staining, and are configured such that the client may click and enlarge to a desired size to be observed.

Here, the discrimination index may be determined in various methods, and it may be determined in consideration of characteristic factors of the bone marrow. For example, the discrimination index may be determined based on a region that best represents the characteristics of the bone marrow where peripheral blood contamination is minimal among adjacent regions of the bone marrow cells in front of and behind the particles having relatively large sizes.

Therefore, the discrimination index unit 20 according to the embodiment, as illustrated in FIG. 3, classifies the bone marrow images into different classes based on discrimination indices determined based on the size and shape of large particles having a size that is larger than other particles in the vicinity, and the size and shape of megakaryocytes in the zone of interest in front of and behind the large particles on the bone marrow image screen.

The result providing unit 30 provides both the required image and the result discriminated by the discrimination index unit 20, as illustrated in FIG. 6.

The device for supporting bone marrow reading based on image analysis according to an embodiment of the present disclosure having the configuration as described above may classify all the bone marrow images acquired by an imaging means such as CT into a class among different classes corresponding to discrimination indices and provide them. Accordingly, the embodiments of the present disclosure provide advantages of saving labor and time by performing bone marrow reading without microscopic observation, allowing consultation with other experts or remote reading of the bone marrow images at a place such as a central reading center by reading the bone marrow images by discrimination indices reflected with an algorithm for discrimination of bone marrow cells, and providing educational data of a complete image set for the training of bone marrow reading doctors.

The embodiment further includes a database unit 40 in which the plurality of bone marrow images that are classified according to preset discrimination indices are stored. The result providing unit 30 may provide both the data analyzed by the discrimination index unit 20 and the data stored in the database unit 40. Accordingly, since the user can compare and analyze the actually read bone marrow images and the databased bone marrow images, more precise bone marrow reading may be facilitated.

Although various embodiments of the present disclosure have been described above, the present embodiment and the accompanying drawings are merely illustrative of some of the technical ideas included in the present disclosure. It will be apparent that modified examples and specific embodiments that can be inferred by those skilled in the art within the technical ideas included in the specification and drawings of the present disclosure are included in the scope of the present disclosure.

What is claimed is:

1. A device for supporting bone marrow reading based on image analysis, comprising:
    an image acquisition unit that acquires, by an imaging device, a bone marrow image of a subject for bone marrow reading;
    a discrimination index unit that generates a required image from the acquired bone marrow image by image processing and software operation, and classifies the acquired bone marrow image into a class among a plurality of classes corresponding to discrimination indices based on a preset algorithm; and
    a result providing unit that provides the required image and a discrimination result read by the discrimination index unit,
    wherein the required image is generated from the acquired bone marrow image to include a large bone marrow particle that has a size larger than sizes of other bone marrow particles in a vicinity thereof in a whole bone marrow image screen.

2. The device of claim 1, wherein the required image includes the large bone marrow particle and megakaryocytes that are present in a zone of interest in front of and behind the large bone marrow particle.

3. The device of claim 1, wherein the result providing unit provides both the required image and a discrimination index corresponding to a class to which the required image belongs.

4. The device of claim 1, further comprising:
    a database unit that stores a plurality of bone marrow images classified based on preset discrimination indices,
    wherein the result providing unit provides both data analyzed by the discrimination index unit and data stored in the database unit.

5. A method of supporting bone marrow reading based on image analysis, the method comprising:
    acquiring, by an imaging device, a bone marrow image of a subject for bone marrow reading;
    generating a required image from the acquired bone marrow image by image processing;
    classifying the acquired bone marrow image into a class among a plurality of classes that correspond to discrimination indices based on a preset algorithm; and
    providing the required image and a discrimination result,
    wherein the required image is generated from the acquired bone marrow image to include a large bone marrow particle that has a size larger than sizes of other bone marrow particles in a vicinity thereof in a whole bone marrow image screen.

6. The method of claim 5, wherein the required image includes the large bone marrow particle and megakaryocytes that are present in a zone of interest in front of and behind the large bone marrow particle.

7. The method of claim 5, wherein the discrimination result includes a discrimination index that corresponds to a class to which the required image belongs.

8. The method of claim 5, further comprising:
    storing, in a database, a plurality of bone marrow images classified based on preset discrimination indices; and
    providing data from the database along with the required image and the discrimination result.

9. A non-transitory computer readable medium containing program instructions executed by a processor or controller, the program instructions when executed by the processor or controller configured to:
    cause an imaging device to acquire a bone marrow image of a subject for bone marrow reading;
    generate a required image from the acquired bone marrow image by image processing;
    classify the acquired bone marrow image into a class among a plurality of classes that correspond to discrimination indices based on a preset algorithm; and provide the required image and a discrimination result,
wherein the required image is generated from the acquired bone marrow image to include a large bone marrow particle that has a size larger than sizes of other bone marrow particles in a vicinity thereof in a whole bone marrow image screen.

10. The non-transitory computer readable medium of claim 9, wherein the required image includes the large bone marrow particle and megakaryocytes that are present in a zone of interest in front of and behind the large bone marrow particle.

11. The non-transitory computer readable medium of claim 9, wherein the discrimination result includes a discrimination index that corresponds to a class to which the required image belongs.

12. The non-transitory computer readable medium of claim 9, wherein the program instructions are further configured to:
  store, in a database, a plurality of bone marrow images classified based on preset discrimination indices; and
  provide data from the database along with the required image and the discrimination result.

* * * * *